United States Patent
Kim et al.

(10) Patent No.: US 12,022,865 B2
(45) Date of Patent: Jul. 2, 2024

(54) CARTRIDGE AND AEROSOL GENERATING DEVICE COMPRISING THE SAME

(71) Applicant: KT&G CORPORATION, Daejeon (KR)

(72) Inventors: Dong Sung Kim, Seoul (KR); Won Kyeong Lee, Gyeonggi-do (KR); Heon Jun Jeong, Seoul (KR); Jae Sung Choi, Gyeonggi-do (KR)

(73) Assignee: KT&G CORPORATION, Daejeon (KR)

( * ) Notice: Subject to any disclaimer, the term of this patent is extended or adjusted under 35 U.S.C. 154(b) by 529 days.

(21) Appl. No.: 17/292,879

(22) PCT Filed: Feb. 8, 2021

(86) PCT No.: PCT/KR2021/001614
§ 371 (c)(1),
(2) Date: May 11, 2021

(87) PCT Pub. No.: WO2021/246613
PCT Pub. Date: Dec. 9, 2021

(65) Prior Publication Data
US 2022/0287361 A1  Sep. 15, 2022

(30) Foreign Application Priority Data
Jun. 5, 2020 (KR) .................. 10-2020-0068598

(51) Int. Cl.
*A24F 40/05* (2020.01)
*A24F 40/10* (2020.01)
(Continued)

(52) U.S. Cl.
CPC .............. *A24F 40/05* (2020.01); *A24F 40/10* (2020.01); *A24F 40/42* (2020.01); *A24F 40/44* (2020.01);
(Continued)

(58) Field of Classification Search
CPC .......... A24F 40/05; A24F 40/10; A24F 40/42; A24F 40/44; A24F 40/485;
(Continued)

(56) References Cited

U.S. PATENT DOCUMENTS 11,039,640 B2 * 6/2021 Liu .................... B05B 17/06
11,324,253 B2 * 5/2022 Liu .................... A24F 40/05
(Continued)

FOREIGN PATENT DOCUMENTS

CN  206043451 U  3/2017
CN  209463300 U  10/2019
(Continued)

OTHER PUBLICATIONS

Extended European Search Report dated Mar. 11, 2022 in Application No. 21722364.3.
(Continued)

*Primary Examiner* — Alexander Gilman
(74) *Attorney, Agent, or Firm* — Sughrue Mion, PLLC

(57) ABSTRACT

Provided is a cartridge for an aerosol generating device, comprising: a mouthpiece having a discharge hole; a liquid storage configured to accommodate an aerosol generating material; a vibrator accommodation space configured to accommodate a vibrator of a main body of the aerosol generating device when the cartridge is coupled to the main body; and a liquid delivery member configured to deliver the aerosol generating material accommodated in the liquid storage to the vibrator accommodation space such that aerosols are generated from the aerosol generating material by vibration of the vibrator accommodated in the vibrator accommodation space.

14 Claims, 8 Drawing Sheets

(51) Int. Cl.
*A24F 40/42* (2020.01)
*A24F 40/44* (2020.01)
*A24F 40/485* (2020.01)
*B05B 17/00* (2006.01)
*B05B 17/06* (2006.01)

(52) U.S. Cl.
CPC ........ *A24F 40/485* (2020.01); *B05B 17/0646* (2013.01); *B05B 17/0676* (2013.01)

(58) Field of Classification Search
CPC ............ B05B 17/0646; B05B 17/0676; B05B 17/0607; A61M 11/005; A61M 15/06
USPC .......................................................... 131/329
See application file for complete search history.

(56) References Cited

U.S. PATENT DOCUMENTS

| | | | | |
|---|---|---|---|---|
| 2015/0282530 A1* | 10/2015 | Johnson | ................ | A24F 40/485 |
| | | | | 392/394 |
| 2017/0119059 A1* | 5/2017 | Zuber | ..................... | A24F 40/46 |
| 2017/0231274 A1* | 8/2017 | Davis | ................... | B65B 39/004 |
| | | | | 141/2 |
| 2017/0341850 A1* | 11/2017 | Sebastian | ................ | A24F 40/30 |
| 2018/0027880 A1* | 2/2018 | Dong | ..................... | F16K 31/50 |
| 2019/0031407 A1* | 1/2019 | Biel | ..................... | B65D 71/502 |
| 2020/0060336 A1* | 2/2020 | Liu | ......................... | A24F 40/40 |
| 2020/0253279 A1* | 8/2020 | Liu | ......................... | A24F 40/05 |
| 2021/0052014 A1* | 2/2021 | Hejazi | ................... | A61M 11/04 |
| 2021/0106774 A1* | 4/2021 | Ezeoke | ............... | A61M 11/042 |
| 2021/0212370 A1* | 7/2021 | Moloney | ............... | A24F 40/485 |
| 2021/0235768 A1* | 8/2021 | Akao | ...................... | A24F 40/53 |
| 2021/0267283 A1* | 9/2021 | Kozlowski | .............. | A24F 40/90 |
| 2022/0007726 A1* | 1/2022 | Ono | ........................ | A24F 40/46 |
| 2022/0007741 A1* | 1/2022 | Ono | ........................ | A24F 40/10 |
| 2022/0014097 A1* | 1/2022 | Ono | ........................ | A24F 40/30 |

FOREIGN PATENT DOCUMENTS

| | | |
|---|---|---|
| CN | 209732616 U | 12/2019 |
| EP | 3251531 A1 | 12/2017 |
| JP | 2019-524120 A | 9/2019 |
| KR | 20-2014-0001494 U | 3/2014 |
| KR | 10-2018-0079298 A | 7/2018 |
| KR | 10-2018-0129929 A | 12/2018 |
| KR | 10-2019-0084312 A | 7/2019 |
| KR | 10-2020-0060467 A | 5/2020 |
| WO | 2016/128562 A1 | 8/2016 |
| WO | 2019/057939 A1 | 3/2019 |
| WO | 2019-122876 A1 | 6/2019 |
| WO | 2019-219865 A1 | 11/2019 |
| WO | 2021/210777 A1 | 10/2021 |

OTHER PUBLICATIONS

International Search Report dated Jul. 19, 2021 in International Application No. PCT/KR2021/001614.
Office Action dated Oct. 4, 2022 from the Japanese Patent Office in Application No. 2021-540449.
Office Action dated Jan. 21, 2022 in Korean Application No. 10-2020-0068598.

* cited by examiner

2

CARTRIDGE AND AEROSOL GENERATING DEVICE COMPRISING THE SAME

CROSS REFERENCE TO RELATED APPLICATIONS

This application is a National Stage of International Application No. PCT/KR2021/001614 filed on Feb. 8, 2021, claiming priority based on Korean Patent Application No. 10-2020-0068598 filed on Jun. 5, 2020.

TECHNICAL FIELD

One or more embodiments relate to a cartridge and an aerosol generating device including the same, and more particularly, to a cartridge that may generate aerosols by using ultrasonic waves, and an aerosol generating device including the cartridge.

BACKGROUND ART

Recently, the demand for an alternative to traditional combustive cigarettes has increased. For example, there is growing demand for a device that generates aerosols by heating an aerosol generating material. Accordingly, studies have been actively conducted on a heating-type cigarette or a heating-type aerosol generating device.

DISCLOSURE OF INVENTION

Technical Problem

One or more embodiments provide an aerosol generating device that may generate aerosols from an aerosol generating material by using a vibrator that generates high frequency vibration such as ultrasonic waves. In addition, one or more embodiments provide an aerosol generating device that may be continuously used by replacing only a cartridge after an aerosol generating material is exhausted.

Technical problems to be solved by the embodiments are not limited to the above-described problems, and problems that are not mentioned will be clearly understood by those of ordinary skill in the art from the present disclosure and the accompanying drawings.

Solution to Problem

According to an aspect of the present disclosure, a cartridge for an aerosol generating device may include: a mouthpiece having a discharge hole; a liquid storage configured to accommodate an aerosol generating material; a vibrator accommodation space configured to accommodate a vibrator of a main body of the aerosol generating device when the cartridge is coupled to the main body; and a liquid delivery member configured to deliver the aerosol generating material accommodated in the liquid storage to the vibrator accommodation space such that aerosols are generated from the aerosol generating material by vibration of the vibrator accommodated in the vibrator accommodation space.

According to another aspect of the present disclosure, an aerosol generating device may include a main body comprising a vibrator configured to generate vibration; and a cartridge detachably coupled to the main body, wherein the cartridge comprises: a mouthpiece having a discharge hole; a liquid storage configured to accommodate an aerosol generating material; a vibrator accommodation space configured to accommodate the vibrator of the main body; and a liquid delivery member configured to deliver the aerosol generating material accommodated in the liquid storage to the vibrator accommodation space such that aerosols are generated from the aerosol generating material by vibration of the vibrator accommodated in the vibrator accommodation space.

Advantageous Effects of Invention

In an aerosol generating device according to embodiments, a main body including a vibrator and a cartridge storing an aerosol generating material may be separately configured, so that the aerosol generating device may be re-used by replacing the cartridge. Accordingly, a user may continue to use the aerosol generating device by simply replacing the cartridge.

In addition, because aerosols may be generated in a non-heating manner by using a vibrator, harmfulness may be reduced in a process of generating aerosols.

Technical problems to be solved by the embodiments are not limited to the above-described problems, and problems that are not mentioned will be clearly understood by those of ordinary skill in the art from the present disclosure and the accompanying drawings.

BEST MODE FOR CARRYING OUT THE INVENTION

Figure 1:
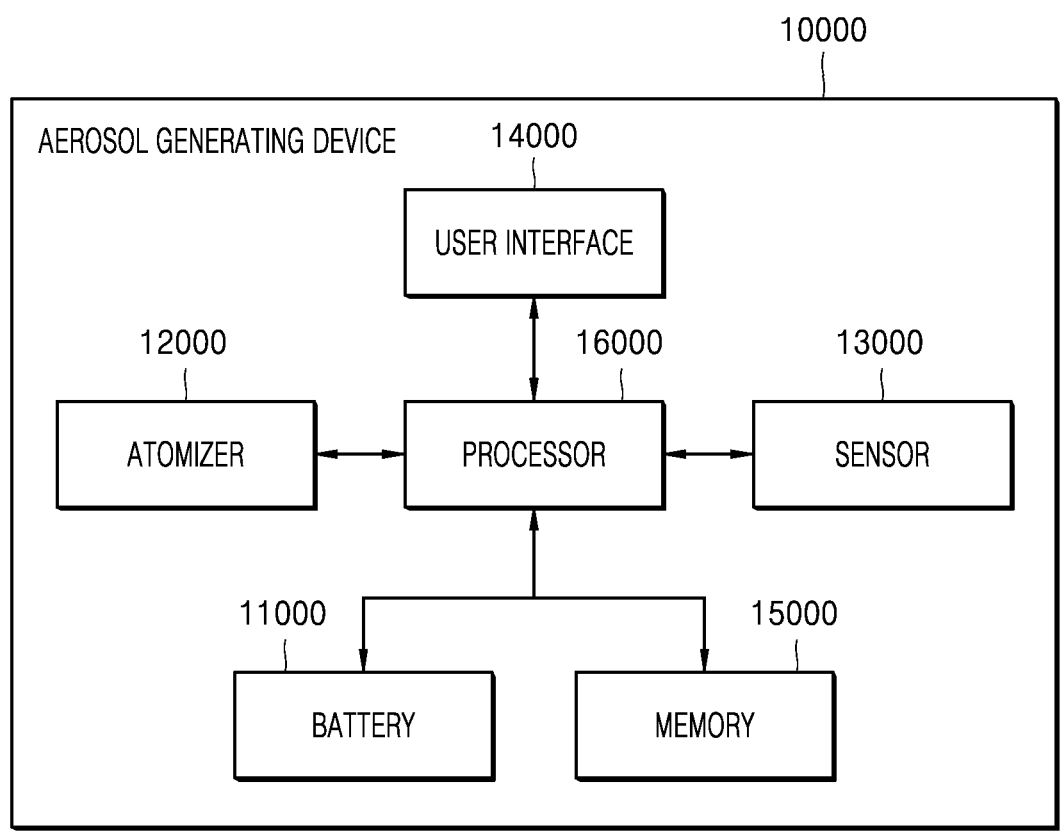
FIG. 1 is a block diagram of an aerosol generating device according to an embodiment.

A cartridge according to an embodiment may include a mouthpiece having a discharge hole; a liquid storage configured to accommodate an aerosol generating material; a vibrator accommodation space configured to accommodate a vibrator of a main body of the aerosol generating device when the cartridge is coupled to the main body; and a liquid delivery member configured to deliver the aerosol generating material accommodated in the liquid storage to the vibrator accommodation space such that aerosols are generated from the aerosol generating material by vibration of the vibrator accommodated in the vibrator accommodation space.

In addition, the liquid delivery member may contact the vibrator when the main body and the cartridge are coupled.

In addition, the cartridge may further include a mesh structure stacked on the liquid delivery member and having a plurality of holes through which aerosols pass to move to the discharge hole.

In addition, the mesh structure may vibrate together with the vibrator.

In addition, the mesh structure may have a form of a metal flat plate.

In addition, the cartridge may further include a conduit connected to the discharge hole of the mouthpiece and forming an aerosol discharge passage through which the aerosols generated by the vibration move toward the discharge hole.

In addition, the conduit may have a cross-sectional area decreasing along a direction from the vibrator accommodation space toward the discharge hole.

In addition, the cartridge may further include a housing comprising a bottom surface and an outer wall, wherein the bottom surface comprises an opening which forms the vibrator accommodation space, wherein the outer wall is connected to the mouthpiece, and wherein the housing forms an exterior of the cartridge with the mouthpiece.

In addition, the cartridge may further include a fixing member attached to the conduit, penetrating at least a portion of the liquid delivery member, and coupled to the housing.

In addition, the liquid storage may include an inner space formed between the housing and the conduit.

In addition, a gap may be formed between the cartridge and the main body when the cartridge is coupled to the main body, such that external air is introduced through the gap.

An aerosol generating device according to another embodiment may include a main body including a vibrator configured to generate vibration and a cartridge that is detachably coupled to the main body, wherein the cartridge may include a mouthpiece having a discharge hole, a liquid storage configured to accommodate an aerosol generating material, a vibrator accommodation space configured to accommodate the vibrator of the main body, and a liquid delivery member configured to deliver the aerosol generating material accommodated in the liquid storage to the vibrator accommodation space such that aerosols may be generated by vibration of the vibrator accommodated in the vibrator accommodation space.

In addition, the main body may further include a first magnetic body, and the cartridge may further include a second magnetic body magnetically coupled to the first magnetic body.

In addition, the main body may further include a battery, a processor configured to control power supplied to the vibrator from the battery, and a connector configured to transfer power of the battery, wherein the connector may include a contact member in contact with the vibrator and an elastic member connected to the contact member.

MODE FOR THE INVENTION

With respect to the terms used to describe the various embodiments, general terms which are currently and widely used are selected in consideration of functions of structural elements in the various embodiments of the present disclosure. However, meanings of the terms can be changed according to intention, a judicial precedence, the appearance of new technology, and the like. In addition, in certain cases, a term which is not commonly used can be selected. In such a case, the meaning of the term will be described in detail at the corresponding portion in the description of the present disclosure. Therefore, the terms used in the various embodiments of the present disclosure should be defined based on the meanings of the terms and the descriptions provided herein.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will be understood that when an element or layer is referred to as being "over," "above," "on," "connected to" or "coupled to" another element or layer, it can be directly over, above, on, connected or coupled to the other element or layer or intervening elements or layers may be present. In contrast, when an element is referred to as being "directly over," "directly above," "directly on," "directly connected to" or "directly coupled to" another element or layer, there are no intervening elements or layers present. Like numerals refer to like elements throughout.

The term "aerosol generating article" may refer to an article containing an aerosol generating material, and its shape, size, material, color, and structure may differ according to embodiments. For example, a cigarette-shaped substrate (hereinafter "cigarette") and/or a cartridge may be used as the aerosol generating article.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and/or operation and can be implemented by hardware components or software components and combinations thereof.

Hereinafter, the present disclosure will now be described more fully with reference to the accompanying drawings, in which exemplary embodiments of the present disclosure are shown such that one of ordinary skill in the art may easily work the present disclosure. The disclosure may, however, be embodied in many different forms and should not be construed as being limited to the embodiments set forth herein.

Hereinafter, embodiments of the present disclosure will be described in detail with reference to the drawings.

FIG. 1 is a block diagram of an aerosol generating device according to an embodiment.

Referring to FIG. 1, an aerosol generating device 10000 may include a battery 11000, an atomizer 12000, a sensor 13000, a user interface 14000, a memory 15000, and a processor 16000. However, the internal structure of the aerosol generating device 10000 is not limited to the structure shown in FIG. 1. According to the design of the aerosol generating device 10000, it will be understood by one of ordinary skill in the art that some of the hardware components shown in FIG. 1 may be omitted or new components may be added.

In an embodiment, the aerosol generating device 10000 may consist of only a main body, and hardware components of the aerosol generating device 10000 may be located in the main body. In another embodiment, the aerosol generating device 10000 may consist of a main body and a cartridge, and hardware components of the aerosol generating device 10000 may be located separately in the main body and the cartridge in a distributed manner. Also, at least some of hardware components of the aerosol generating device 10000 may be located in both the main body and the cartridge.

Hereinafter, an operation of each of the components will be described without limiting locations of the components of the aerosol generating device 10000.

The battery 11000 supplies electric power to be used for the aerosol generating device 10000 to operate. That is, the battery 11000 may supply power so that the atomizer 12000 may atomize an aerosol generating material. In addition, the battery 11000 may supply power required for operations of other hardware components included in the aerosol generating device 10000, that is, the sensor 13000, the user interface 14000, the memory 15000, and the processor 16000. The battery 11000 may be a rechargeable battery or a disposable battery.

For example, the battery 11000 may include a nickel-based battery (for example, a nickel-metal hydride battery or a nickel-cadmium battery) or a lithium-based battery (for example, a lithium-cobalt battery, a lithium-phosphate battery, a lithium-titanate battery, a lithium-ion battery, or a lithium-polymer battery). However, a type of the battery 11000 which may be used in the aerosol generating device 10000 is not limited thereto. When needed, the battery 11000 may include an alkaline battery or a manganese battery.

The atomizer 12000 receives power from the battery 11000 under the control of the processor 16000. The atomizer 12000 may receive power from the battery 11000 to atomize an aerosol generating material stored in the aerosol generating device 10000.

The atomizer 12000 may be located in the main body of the aerosol generating device 10000. Alternatively, if the aerosol generating device 10000 includes the main body and the cartridge, the atomizer 12000 may be located in the cartridge or may be separately located in the main body and the cartridge. When the atomizer 12000 is located in the cartridge, the atomizer 12000 may receive power from the battery 11000 located in at least one of the main body and the cartridge. In addition, when the atomizer 12000 is separately located in the main body and the cartridge, components that require power in the atomizer 12000 may receive power from the battery 11000 located in at least one of the main body and the cartridge.

The atomizer 12000 generates aerosols from an aerosol generating material inside the cartridge. Aerosols refer to a floating matter in which liquid and/or solid fine particles are dispersed in a gas. Accordingly, aerosols generated from the atomizer 12000 may mean a state in which vaporized particles generated from an aerosol generating material and air are mixed. For example, the atomizer 12000 may convert a phase of the aerosol generating material into a gaseous phase through vaporization and/or sublimation. In addition, the atomizer 12000 may generate aerosols by granulating and discharging the aerosol generating material in a liquid and/or solid state.

For example, the atomizer 12000 may generate aerosols from the aerosol generating material by using an ultrasonic-wave vibration method. The ultrasonic-wave vibration method may mean a method of generating aerosols by atomizing an aerosol generating material with ultrasonic-wave vibration generated by a vibrator.

Although not illustrated in FIG. 1, in an embodiment, the atomizer 12000 may include a heater for heating an aerosol generating material. The aerosol generating material may be heated by the heater, thereby generating aerosols.

The heater may be formed of any suitable electrically resistive material. For example, the suitable electrically resistive material may be a metal or a metal alloy including titanium, zirconium, tantalum, platinum, nickel, cobalt, chromium, hafnium, niobium, molybdenum, tungsten, tin, gallium, manganese, iron, copper, stainless steel, or nichrome, but is not limited thereto. In addition, the heater may be implemented by a metal wire, a metal plate on which an electrically conductive track is arranged, a ceramic heating element, or the like, but is not limited thereto.

Figure 2:
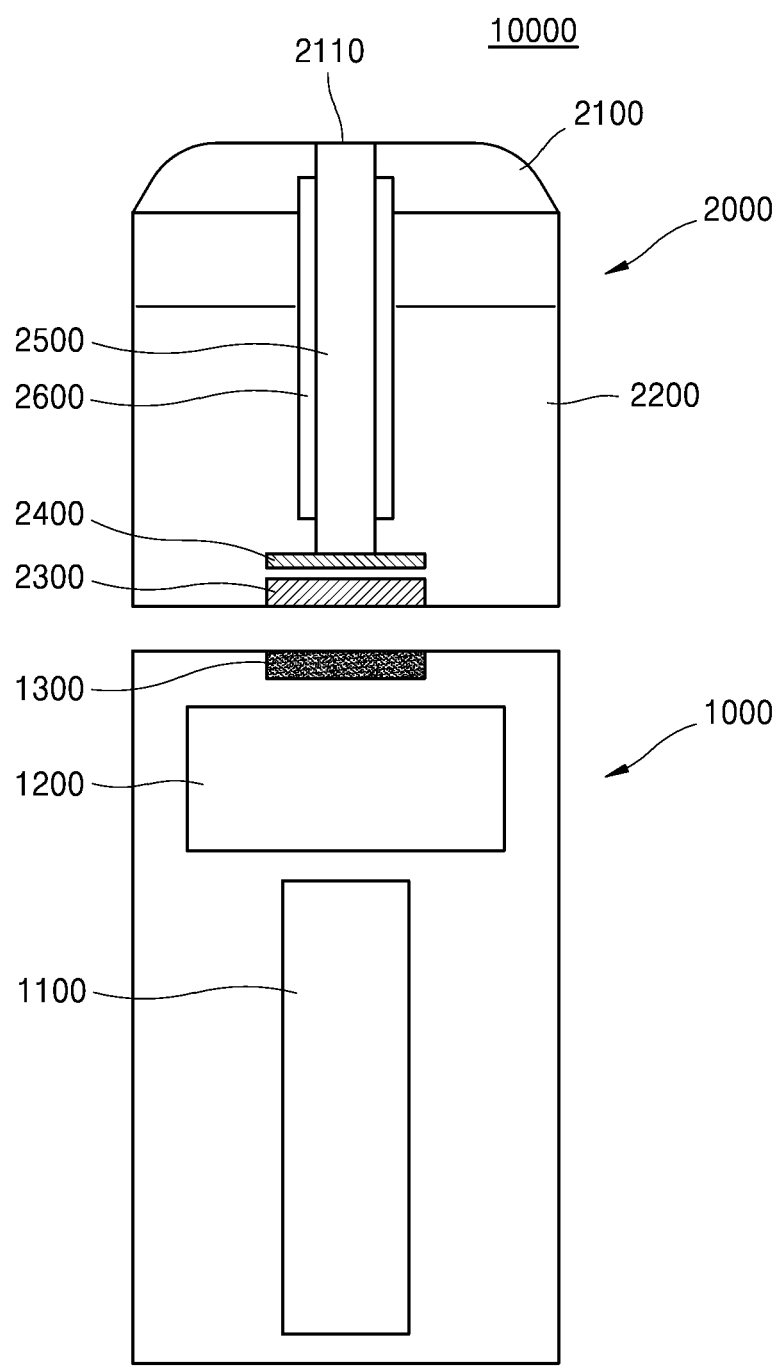
FIG. 2 is a schematic diagram of an aerosol generating device according to an embodiment.

For example, according to an embodiment, the heater may be a component included in a cartridge 2000 in FIG. 2. In addition, the cartridge 2000 may include a liquid delivery element and a liquid storage to be described below. An aerosol generating material accommodated in the liquid storage may be moved to the liquid delivery element, and the heater may heat the aerosol generating material absorbed by the liquid delivery element, thereby generating aerosols. For example, the heater may be wound around the liquid delivery element or arranged adjacent to the liquid delivery element.

In another embodiment, the aerosol generating device 10000 may include an accommodation space that may accommodate a cigarette, and the heater may heat the cigarette inserted into the accommodation space of the aerosol generating device 10000. As the cigarette is accommodated in the accommodation space of the aerosol generating device 10000, the heater may be located inside and/or outside the cigarette. Accordingly, the heater may cause the cigarette to generate aerosols by heating an aerosol generating material in the cigarette.

The heater may include an induction heater. The heater may include an electrically conductive coil for heating a cigarette or a cartridge in an induction heating method, and the cigarette or the cartridge may include a susceptor which may be heated by the induction heater.

The aerosol generating device 10000 may include at least one sensor 13000. A result sensed by the at least one sensor 13000 may be transmitted to the processor 16000, and the processor 16000 may control the aerosol generating device 10000 to perform various functions such as controlling an operation of the atomizer 12000, restricting smoking, determining whether a cartridge (or a cigarette) is inserted, displaying a notification, or the like, according to the sensed result.

For example, the at least one sensor 13000 may include a puff detection sensor. The puff detection sensor may sense a user's puff based on at least one of a flow change of an airflow introduced from the outside, a pressure change, and sensing of sound. The puff detection sensor may sense a start timing and an end timing of a user's puff, and the puff detection sensor may determine a puff period and a non-puff period according to the sensed start timing and the end timing of a puff.

In addition, the at least one sensor 13000 may include a user input sensor, such as a switch, a physical button, a touch sensor, or the like, which detects a user's input. For example, the touch sensor may be a capacitive sensor that may sense the user's input by sensing a change in capacitance that occurs when a user touches a certain area formed of a metallic material. The processor 16000 may determine whether the user's input has occurred based on the change in the capacitance value received from the capacitive sensor. When a change in the capacitance value is greater than a preset threshold value, the processor 16000 may determine that the user's input has occurred.

In addition, the at least one sensor 13000 may include a motion sensor. Information about a movement of the aerosol generating device 10000, such as an incline, movement speed, acceleration, or the like of the aerosol generating device 10000, may be obtained through the motion sensor. For example, the motion sensor may measure information about a state in which the aerosol generating device 10000 moves, a stationary state of the aerosol generating device 10000, a state in which the aerosol generating device 10000 is inclined at an angle with a certain range for a puff, and a state in which the aerosol generating device 10000 is inclined at an angle different from that during puff operation between each puff operation. The motion sensor may measure motion information of the aerosol generating device 10000 by using various methods known in the art. For example, the motion sensor may include an acceleration sensor capable of measuring acceleration in three directions of x-axis, y-axis, and z-axis, and a gyro sensor capable of measuring an angular speed in three directions.

In addition, the at least one sensor 13000 may include a proximity sensor. The proximity sensor refers to a sensor that detects the presence or distance of an approaching object or an object in the vicinity by using a force of an electromagnetic field, infrared light, or the like, without mechanical contact. Accordingly, it is possible to detect whether a user is approaching the aerosol generating device 10000.

In addition, the at least one sensor 13000 may include an image sensor. For example, the image sensor may include a camera configured to obtain an image of an object. The image sensor may recognize an object based on an image obtained by the camera. The processor 16000 may determine whether a user is in a situation for using the aerosol generating device 10000 by analyzing an image obtained through the image sensor. For example, when the user approaches the aerosol generating device 10000 near his/her lips to use the aerosol generating device 10000, the image sensor may obtain an image of the lips. The processor 16000 may analyze the obtained image and determine that the user is about to use the aerosol generating device 10000 when the obtained image is determined as lips. Accordingly, the aerosol generating device 10000 may operate atomizer 12000 in advance, or may preheat the heater.

In addition, the at least one sensor 13000 may include a consumable attachment and detachment sensor which may sense the mounting or removal of a consumable (for example, a cartridge, a cigarette, or the like) that may be used in the aerosol generating device 10000. For example, the consumable attachment and detachment sensor may sense whether the consumable has contacted the aerosol generating device 10000, or determine whether the consumable is mounted or removed by the image sensor. In addition, the consumable attachment and detachment sensor may be an inductance sensor that senses a change in an inductance value of a coil which may interact with a marker of a consumable or a capacitance sensor that senses a change in a capacitance value of a capacitor which may interact with a marker of a consumable.

In addition, the at least one sensor 13000 may include a temperature sensor. The temperature sensor may sense a temperature at which the heater (or an aerosol generating material) of the atomizer 12000 is heated. The aerosol generating device 10000 may include a separate temperature sensor sensing a temperature of the heater, or the heater itself may serve as a temperature sensor instead of including a separate temperature sensor. Alternatively, a separate temperature sensor may be further included in the aerosol generating device 10000 while the heater serves as a temperature sensor. In addition, the temperature sensor may sense not only the temperature of the heater but also the temperature of internal components such as a printed circuit board (PCB), a battery, or the like of the aerosol generating device 10000.

In addition, the at least one sensor 13000 may include various sensors that measure information about a surrounding environment of the aerosol generating device 10000. For example, the at least one sensor 13000 may include a temperature sensor that may measure a temperature of a surrounding environment, a humidity sensor that measures a humidity of a surrounding environment, an atmospheric pressure sensor that measures a pressure of a surrounding environment, or the like.

The sensor 13000 in the aerosol generating device 10000 is not limited to the above-stated types, and may further include various sensors. For example, the aerosol generating device 10000 may include a fingerprint sensor that may obtain fingerprint information from a user's finger for user authentication and security, an iris recognition sensor analyzing an iris pattern of a pupil, a vein recognition sensor that senses absorption of infrared rays of reduced hemoglobin in veins from an image capturing a palm, a face recognition sensor that recognizes feature points such as eyes, nose, mouth, facial contours, or the like in a two-dimensional (2D) or three-dimensional (3D) method, a radio-frequency identification (RFID) sensor, or the like.

The aerosol generating device 10000 may include one or more of the above-described various sensors 13000. In other words, the aerosol generating device 10000 may combine and use information sensed by at least one of the above-described sensors.

The user interface 14000 may provide the user with information about the state of the aerosol generating device 10000. The user interface 14000 may include various interfacing devices, such as a display or a lamp for outputting visual information, a motor for outputting haptic information, a speaker for outputting sound information, input/output (I/O) interfacing devices (for example, a button or a touch screen) for receiving information input from the user or outputting information to the user, terminals for performing data communication or receiving charging power, and communication interfacing modules for performing wireless communication (for example, Wi-Fi, Wi-Fi direct. Bluetooth, near-field communication (NFC), etc.) with external devices.

According to embodiments, the aerosol generating device 10000 may be implemented by selecting only some of the above-described various interfacing devices.

The memory 15000 may be a hardware component configured to store various pieces of data processed in the aerosol generating device 10000, and the memory 15000 may store data processed or to be processed by the processor 16000. The memory 15000 may include various types of memories, such as random access memory (RAM), such as dynamic random access memory (DRAM), static random access memory (SRAM), etc., read-only memory (ROM), electrically erasable programmable read-only memory (EEPROM), etc.

The memory 15000 may store an operation time of the aerosol generating device 10000, the maximum number of puffs, the current number of puffs, at least one temperature profile, data on a user's smoking pattern, etc.

The processor 16000 controls general operations of the aerosol generating device 10000. The processor 16000 may be implemented as an array of a plurality of logic gates or may be implemented as a combination of a general-purpose microprocessor and a memory in which a program executable in the microprocessor is stored. It will be understood by one of ordinary skill in the art that the processor may be implemented in other forms of hardware.

The processor 16000 analyzes a result of the sensing by the at least one sensor 13000, and controls processes that are to be performed subsequently.

The processor 16000 may control power supplied to the atomizer 12000 so that the operation of the atomizer 12000 is started or terminated, based on the result of the sensing by the at least one sensor 13000. In addition, based on the result of the sensing by the at least one sensor 13000, the processor 16000 may control the amount of power supplied to the atomizer 12000 and the time at which the power is supplied, so that the atomizer 12000 may generate the appropriate amount of aerosols. For example, the processor 16000 may control a current supplied to a vibrator so that the vibrator of the atomizer 12000 vibrates at a certain frequency.

In an embodiment, the processor 16000 may start the operation of the atomizer 12000 after receiving a user input for the aerosol generating device 10000. In addition, the processor 16000 may start the operation of the atomizer 12000 after sensing a user's puff by using a puff detection sensor. In addition, the processor 16000 may stop supplying power to the atomizer 12000 when the number of puffs counted by the puff detection sensor reaches a preset number.

The processor 16000 may control the user interface 14000 based on the result of the sensing by the at least one sensor 13000. For example, when the number of puffs counted by the puff detection sensor reaches the preset number, the processor 16000 may notify the user by using at least one of a lamp, a motor, and a speaker that the aerosol generating device 10000 will soon be terminated.

Although not illustrated in FIG. 1, an aerosol generating system may be configured by the aerosol generating device 10000 and a separate cradle. For example, the cradle may be used to charge the battery 11000 of the aerosol generating device 10000. For example, the aerosol generating device 10000 may be supplied with power from a battery of the cradle to charge the battery 11000 of the aerosol generating device 10000 while being accommodated in an accommodation space of the cradle.

One embodiment may also be implemented in the form of a computer-readable recording medium including instructions executable by a computer, such as a program module executable by the computer. The computer-readable recording medium may be any available medium that can be accessed by a computer and includes both volatile and nonvolatile media, and removable and non-removable media. In addition, the computer-readable recording medium may include both a computer storage medium and a communication medium. The computer storage medium includes all of volatile and nonvolatile, and removable and non-removable media implemented by any method or technology for storage of information such as computer-readable instructions, data structures, program modules or other data. The communication medium typically includes computer-readable instructions, data structures, other data in modulated data signals such as program modules, or other transmission mechanisms, and includes any information transfer media.

FIG. 2 is a schematic diagram of an aerosol generating device according to an embodiment.

The aerosol generating device 10000 according to an embodiment shown in FIG. 2 includes the cartridge 2000 containing an aerosol generating material and a main body 1000 supporting the cartridge 2000.

The cartridge 2000 may be coupled to the main body 1000 in a state in which the aerosol generating material is accommodated therein. For example, as a portion of the cartridge 2000 is inserted into the main body 1000 or a portion of the main body 1000 is inserted into the cartridge 2000, the cartridge 2000 may be mounted on the main body 1000. For example, the main body 1000 and the cartridge 2000 may be maintained in a coupled stated by a snap-fit method, a screw coupling method, a magnetic coupling method, an interference fit method, or the like, but the coupling method of the main body 1000 and the cartridge 2000 is not limited by the above-stated methods.

The cartridge 2000 may include a mouthpiece 2100. The mouthpiece 2100 may be inserted into the user's oral cavity and may be formed on the opposite side from a portion coupled to the main body 1000. The mouthpiece 2100 may include a discharge hole 2110 for discharging aerosols generated from the aerosol generating material of the cartridge 2000 to the outside.

The cartridge 2000 may contain an aerosol generating material in any one of, for example, a liquid state, a solid state, a gaseous state, a gel state, or the like. The aerosol generating material may include a liquid composition. For example, the liquid composition may be a liquid including a tobacco-containing material having a volatile tobacco flavor component, or a liquid including a non-tobacco material.

For example, the liquid composition may include one or more components of water, solvents, ethanol, plant extracts, spices, flavorings, and vitamin mixtures. The spices may include menthol, peppermint, spearmint oil, various fruit-flavored ingredients, or the like, but are not limited thereto. The flavorings may include ingredients capable of providing various flavors or tastes to a user. Vitamin mixtures may be a mixture of at least one of vitamin A, vitamin B, vitamin C, and vitamin E, but are not limited thereto. In addition, the liquid composition may include an aerosol forming agent such as glycerin and propylene glycol.

For example, the liquid composition may include glycerin and propylene glycol solution to which nicotine salts are added. The liquid composition may include two or more types of nicotine salts. Nicotine salts may be formed by adding suitable acids, including organic or inorganic acids, to nicotine. Nicotine may be a naturally generated nicotine or synthetic nicotine and may have any suitable weight concentration relative to the total solution weight of the liquid composition.

Acid for the formation of the nicotine salts may be appropriately selected in consideration of the rate of nicotine absorption in the blood, the operating temperature of the aerosol generating device 10000, the flavor or savor, the solubility, or the like. For example, the acid for the formation of nicotine salts may be a single acid selected from the group consisting of benzoic acid, lactic acid, salicylic acid, lauric acid, sorbic acid, levulinic acid, pyruvic acid, formic acid, acetic acid, propionic acid, butyric acid, valeric acid, caproic acid, caprylic acid, capric acid, citric acid, myristic acid, palmitic acid, stearic acid, oleic acid, linoleic acid, linolenic acid, phenylacetic acid, tartaric acid, succinic acid, fumaric acid, gluconic acid, saccharic acid, malonic acid or malic acid, or a mixture of two or more acids selected from the group, but is not limited thereto.

The cartridge 2000 may include a liquid storage 2200 accommodating an aerosol generating material therein. For example, the liquid storage 2200 may function as a container simply holding the aerosol generating material or may include an element, such as a sponge, cotton, fabric, or porous ceramic structure, which is impregnated with (i.e., containing) an aerosol generating material.

The aerosol generating device 10000 may include an atomizer that converts a phase of the aerosol generating material included in the cartridge 2000 to generate aerosols.

For example, the atomizer of the aerosol generating device 10000 may convert the phase of the aerosol generating material by using an ultrasonic-wave vibration method in which the aerosol generating material is atomized with ultrasonic-wave vibration. The atomizer may include a vibrator 1300 for generating ultrasonic-wave vibration, a liquid delivery element 2400 for absorbing the aerosol generating material and maintaining the aerosol generating material in an optimal state for conversion into aerosols, and a vibration accommodation unit 2300 for generating aerosols by transmitting ultrasonic-wave vibration to the aerosol generating material of the liquid delivery element 2400.

The vibrator 1300 may generate vibration having a short period. Vibration generated from the vibrator 1300 may be ultrasonic-wave vibration, and a frequency of the ultrasonic-wave vibration may be, for example, 100 kHz to 3.5 MHz. The aerosol generating material may be vaporized and/or granulated by the short-period vibration generated from the vibrator 1300, thereby being atomized into aerosols.

The vibrator 1300 may include, for example, a piezoelectric ceramic which is a functional material capable of generating electricity (i.e., voltage) by a physical force (i.e., pressure). Conversely, when electricity is applied, the piezoelectric ceramic converts the electricity into vibration (i.e., mechanical force). In other words, vibration (i.e., physical force) may be generated by electricity applied to the vibrator 1300, and the vibration may split the aerosol generating material into small particles and atomize the aerosol generating material into aerosols.

The vibrator 1300 may be in an electrical contact with a circuit by a pogo pin or a C-clip. Accordingly, the vibrator 1300 may receive current from the pogo pin or the C-clip to generate vibration. However, the type of an element connected to supply current to the vibrator 1300 is not limited by the above description.

The vibration accommodation unit 2300 may perform a function of receiving the vibration generated from the vibrator 1300 and converting the aerosol generating material transmitted from the liquid storage 2200 into aerosols.

The liquid delivery element 2400 may deliver a liquid composition of the liquid storage 2200 to the vibration accommodation unit 2300. For example, the liquid delivery element 2400 may be a wick including at least one of a cotton fiber, a ceramic fiber, a glass fiber, a porous ceramic, but is not limited thereto.

In an embodiment, the atomizer may be implemented by a vibration accommodation unit in the form of a mesh shape or plate shape, which performs a function of absorbing and maintaining the aerosol generating material in an optimal state for conversion to aerosols without a need for a separate liquid delivery element, and a function of generating aerosols by transmitting vibration to the aerosol generating material.

In FIG. 2, the vibrator 1300 of the atomizer is arranged in the main body 1000, and the vibration accommodation unit 2300 and the liquid delivery element 2400 are arranged in the cartridge 2000, but embodiments are not limited thereto. For example, the cartridge 2000 may include the vibrator 1300, the vibration accommodation unit 2300, and the liquid delivery element 2400, and when a portion of the cartridge 2000 is inserted into the main body 1000, the main body 1000 may provide, through a terminal (not shown), power to the cartridge 2000, or supply a signal related to the operation of the cartridge 2000 to the cartridge 2000. Accordingly, the operation of the vibrator 1300 may be controlled.

At least a portion of the liquid storage 2200 of the cartridge 2000 may include a transparent material so that the aerosol generating material accommodated in the cartridge 2000 may be visually identified from the outside. The mouthpiece 2100 and the liquid storage 2200 may be entirely or partially formed of a transparent material such as transparent plastic, glass, or the like.

The cartridge 2000 of the aerosol generating device 10000 may include an aerosol discharge passage 2500 and an airflow passage 2600.

The aerosol discharge passage 2500 may be formed inside the liquid storage 2200 and may be in fluid communication with the discharge hole 2110 of the mouthpiece 2100. Accordingly, aerosols generated from the atomizer may move along the aerosol discharge passage 2500 and may be delivered to the user through the discharge hole 2110 of the mouthpiece 2100.

The airflow passage 2600 is a passage through which external air may be introduced into the aerosol generating device 10000. External air introduced through the airflow passage 2600 may be introduced into the aerosol discharge passage 2500, or may be introduced into a space where aerosols are generated. Accordingly, aerosols may be generated by external air mixed with vaporized particles from the aerosol generating material.

For example, as shown in FIG. 2, the airflow passage 2600 may be formed to surround the outside of the aerosol discharge passage 2500. Accordingly, the form of the aerosol discharge passage 2500 and the airflow passage 2600 may be a double-pipe form in which the aerosol discharge passage 2500 is arranged in an inner side and the airflow passage 2600 is arranged outside the aerosol discharge passage 2500. Accordingly, external air may be introduced in a direction opposite to a direction in which aerosols move in the aerosol discharge passage 2500.

The configuration of the airflow passage 2600 is not limited to the above description. For example, the airflow passage 2600 may be a space which is formed between the main body 1000 and the cartridge 2000 and which is in a fluid communication with the atomizer.

In the aerosol generating device 10000 according to the above-described embodiment, cross-sectional shapes of the main body 1000 and the cartridge 2000 when cut in a direction across a longitudinal direction may be substantially circular, elliptical, square, rectangular, or polygonal in various forms. However, the cross-sectional shape of the aerosol generating device 10000 is not limited by the above description. For example, the aerosol generating device 10000 is not necessary limited to a structure that extends linearly when extending in the longitudinal direction, and may be curved in a streamlined shape or bent at a preset angle in a specific area to be easily held by the user. Accordingly, the cross-sectional shapes may change along the longitudinal direction.

Figure 3:
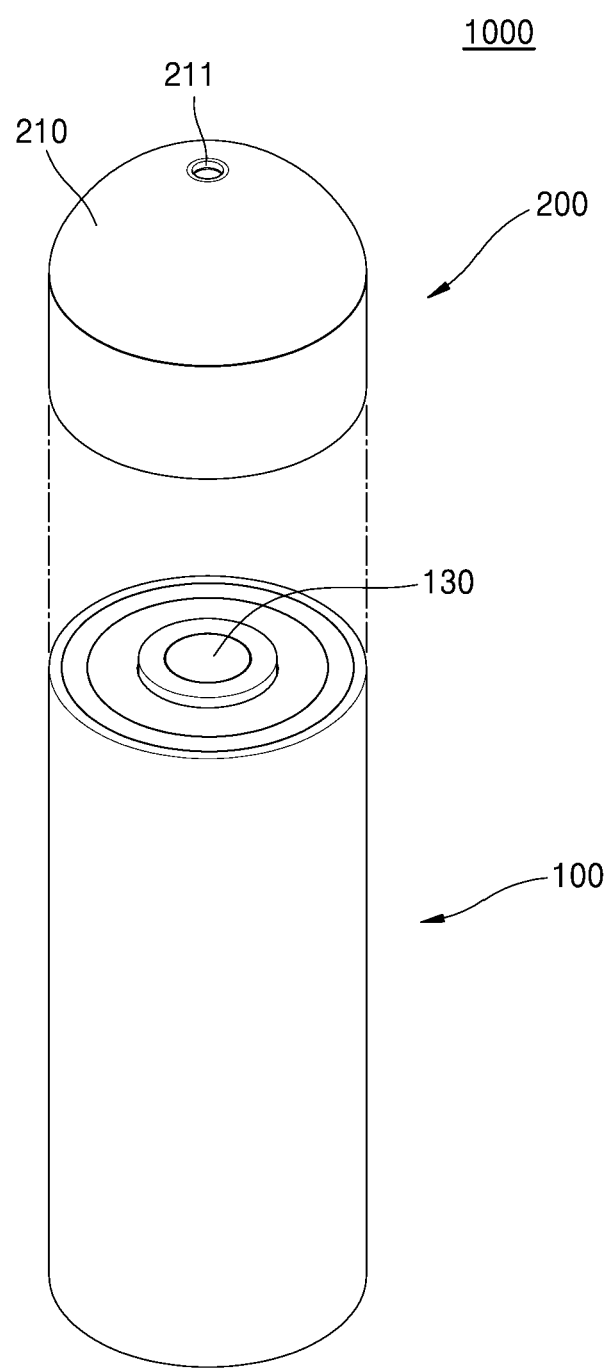
FIG. 3 is a perspective view illustrating a state in which a main body and a cartridge of an aerosol generating device according to an embodiment are separated.
Figure 4:
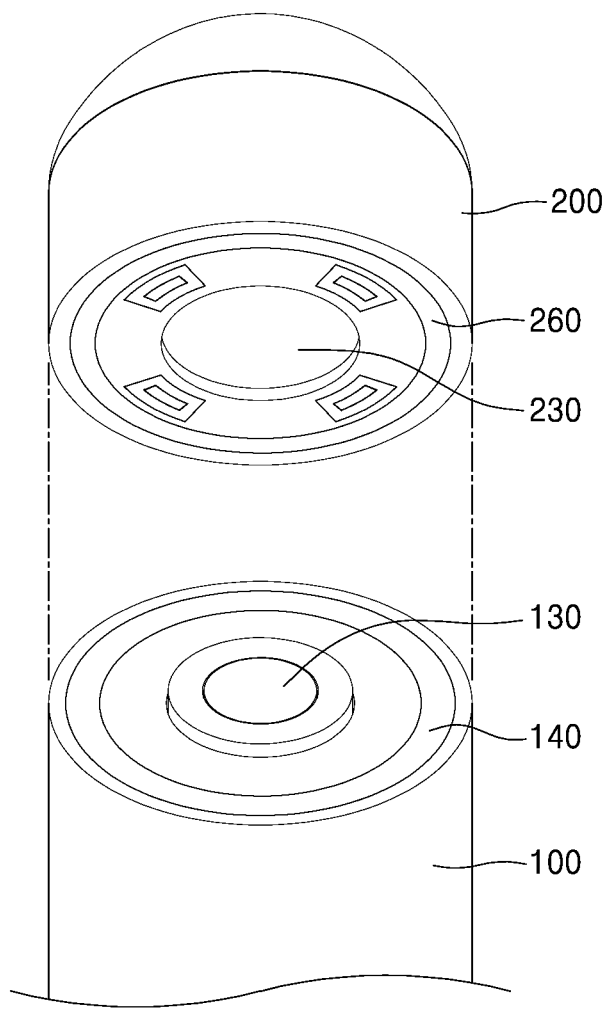
FIG. 4 is a diagram for explaining an example of a method by which a main body and a cartridge are coupled.

FIG. 3 is a perspective view illustrating a state in which a main body and a cartridge of an aerosol generating device according to an embodiment are separated, and FIG. 4 is a diagram for explaining an example of a method by which a main body and a cartridge are coupled.

Hereinafter, even when omitted, contents described with respect to the aerosol generating device 10000 of FIGS. 1 and 2 may also be applied to an aerosol generating device to be described below.

Referring to FIGS. 3 and 4, an aerosol generating device 1000 includes a main body 100 and a cartridge 200 which may be detachably coupled to the main body 100.

The main body 100 may include a vibrator 130 which may generate vibration. The vibrator 130 may protrude from one surface of the main body 100. In addition, the cartridge 200 may include a mouthpiece 210 having a discharge hole 211 and a vibrator accommodation space 230 which may accommodate the vibrator 130 protruding from the main body 100.

Figure 7:
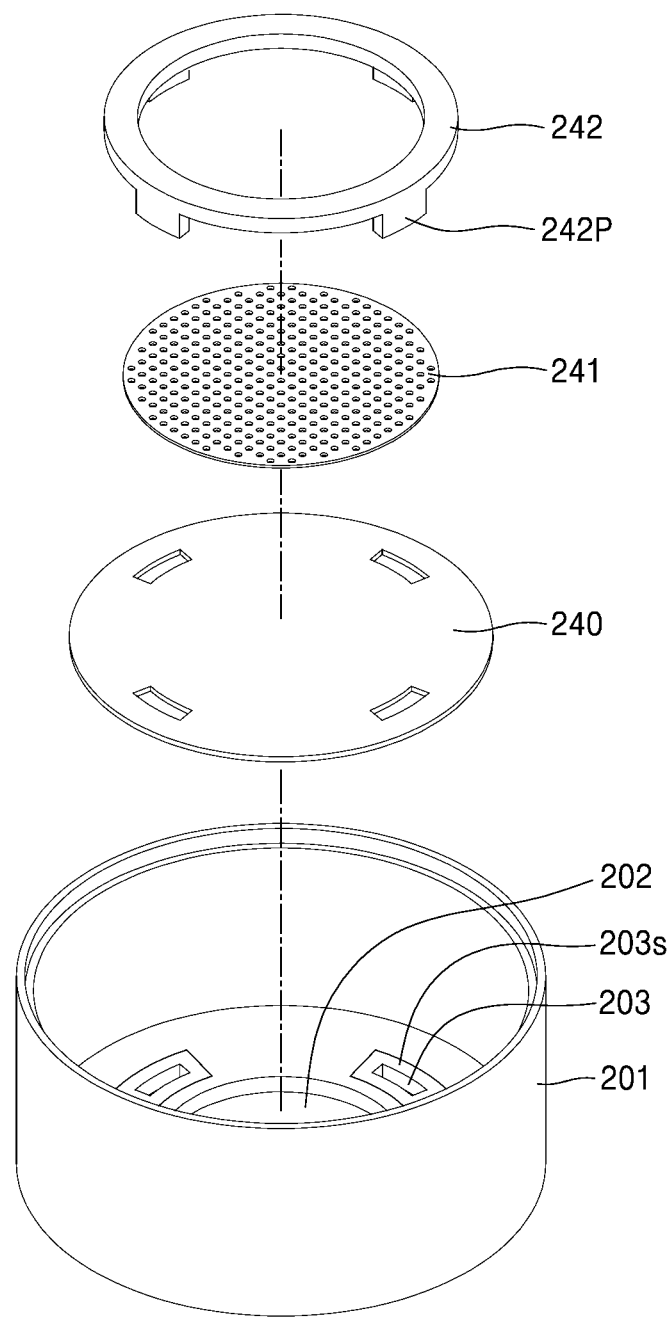
FIG. 7 is a partial exploded view of a cartridge according to an embodiment.

The vibrator accommodation space 230 may have a shape corresponding to a shape of the vibrator 130. Although the vibrator 130 and the vibrator accommodation space 230 are shown in a circular shape in the embodiment shown in FIG. 4, but are not limited to the shape shown. For example, the vibrator 130 may have an elliptical shape or a polygonal shape, and the vibrator accommodation space 230 may have a shape corresponding to the shape of the vibrator 130. The vibrator accommodation space 230 may be formed by an opening 202 of a housing 201 as shown in FIG. 7, and a detailed description thereof will be described below.

To maintain the main body 100 and the cartridge 200 in a coupled state, the main body 100 may include a first magnetic body 140, and the cartridge 200 may include a second magnetic body 260 that is magnetically coupled to the first magnetic body 140 when the cartridge 200 is coupled to the main body 100. For example, the first magnetic body 140 of the main body 100 may have an annular shape surrounding the vibrator 130. Correspondingly, the second magnetic body 260 of the cartridge 200 may have an annular shape to correspond to the first magnetic body 140, and may also be arranged at a position corresponding to the first magnetic body 140.

The first magnetic body 140 and the second magnetic body 260 may include, for example, a permanent magnet or a material such as iron, nickel, chromium, cobalt, an alloy thereof, or the like. In addition, any types of magnets may be used as long as the magnet is capable of generating a magnetic field, such as a neodymium magnet, a rubber magnet, an electromagnet, or the like. The magnet may include samarium, scandium, neodymium, yttrium, or the like. For example, the first magnetic body 140 of the main body 100 may include a magnet, and the second magnetic body 260 of the cartridge 200 may include a stainless steel which may be magnetically coupled to the first magnetic body 140. However, the materials of the first magnetic body 140 and the second magnetic body 260 are not limited to those described above, and any materials that allow the first magnetic body 140 and the second magnetic body 260 to maintain coupling to each other may be used without limitation.

Figure 5:
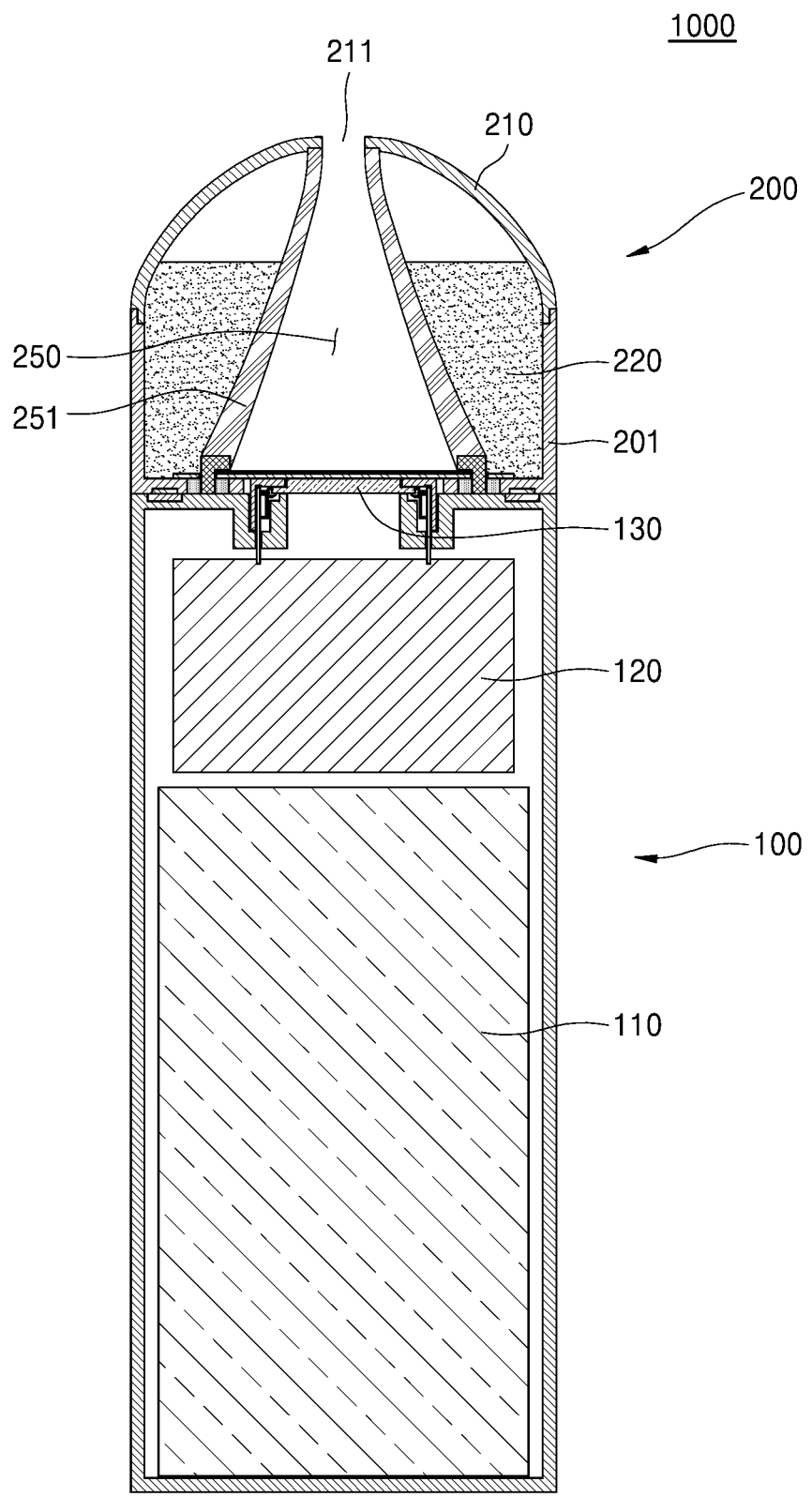
FIG. 5 is a cross-sectional view illustrating a state in which the main body and the cartridge of the aerosol generating device according to the embodiment shown in FIG. 3 are coupled.

FIG. 5 is a cross-sectional view illustrating a state in which the main body and the cartridge of the aerosol generating device according to the embodiment shown in FIG. 3 are coupled.

Referring to FIG. 5, the main body 100 may include a battery 110 and a processor 120 capable of controlling the vibrator 130. In addition, the cartridge 200 may include a housing 201, the mouthpiece 210, a liquid storage 220, and an aerosol discharge passage 250.

The housing 201 may form the exterior of the cartridge 200 together with the mouthpiece 210. The housing 201 may include a bottom surface and an outer wall connected to the mouthpiece 210.

The liquid storage 220 may include an inner space formed between the housing 201 and a conduit 251. The liquid storage 220 may hold an aerosol generating material in the inner space.

One end of the aerosol discharge passage 250 may meet the vibrator accommodation space 230 in which the vibrator 130 is accommodated, and the other end may be connected to the discharge hole 211 of the mouthpiece 210. The aerosol discharge passage 250 may be formed by the conduit 251, and aerosols generated by the vibrator 130 may move through the aerosol discharge passage 250. Aerosols that has moved through the aerosol discharge passage 250 may be discharged to the outside through the discharge hole 211.

The cross-sectional area of the aerosol discharge passage 250 may decrease along a direction from the vibrator accommodation space 230 toward the discharge hole 211. Accordingly, aerosols may move faster as they move in the aerosol discharge passage 250 may increase in speed from the vibrator accommodation space 230 toward the discharge hole 211. Accordingly, the user may inhale the aerosols quickly from the beginning of smoking on the aerosol generating device 1000.

Figure 6A:
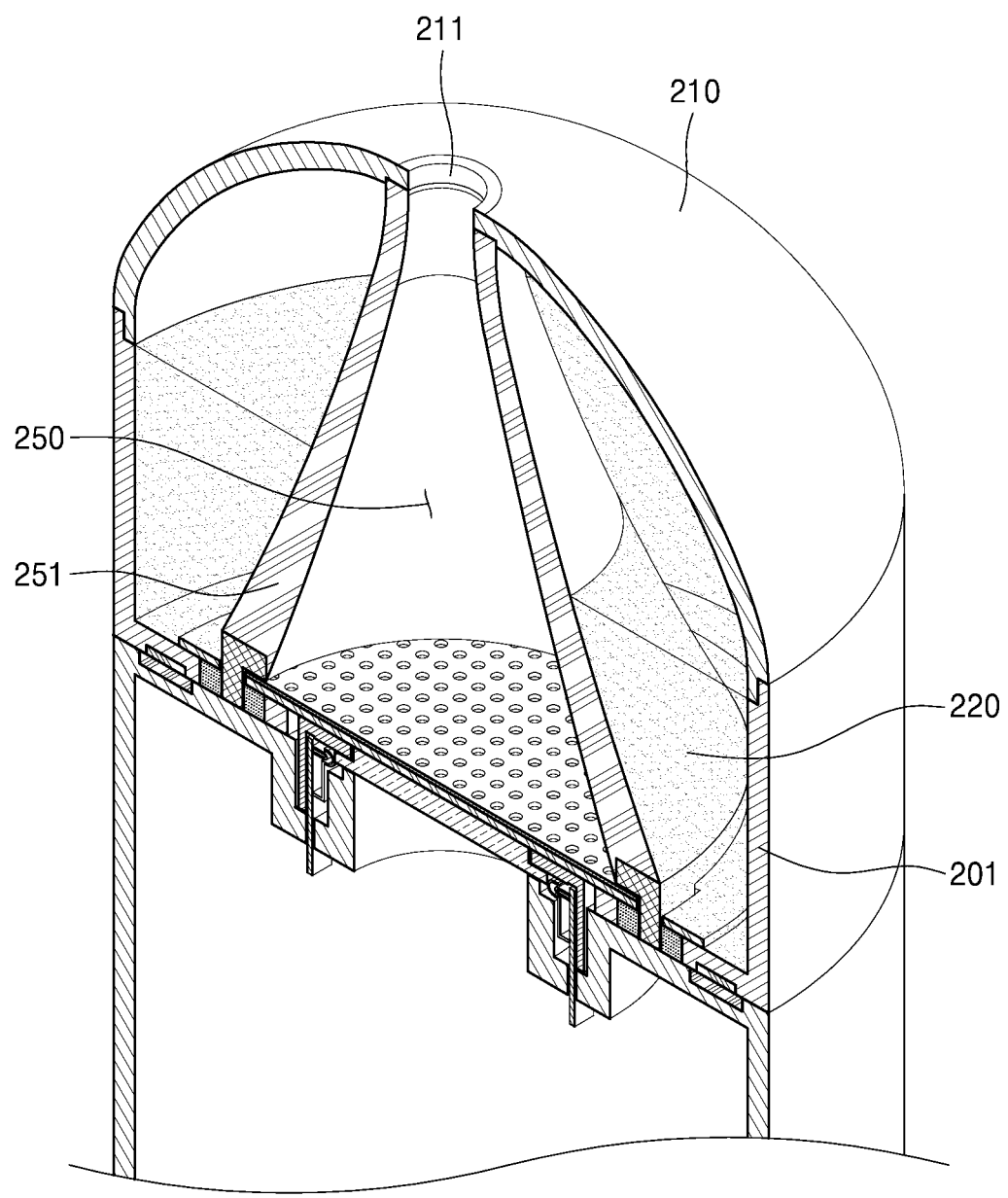
FIG. 6A is an enlarged cross-sectional perspective view of a portion of a cartridge in which aerosols are generated according to an embodiment shown in FIG. 5.
Figure 6B:
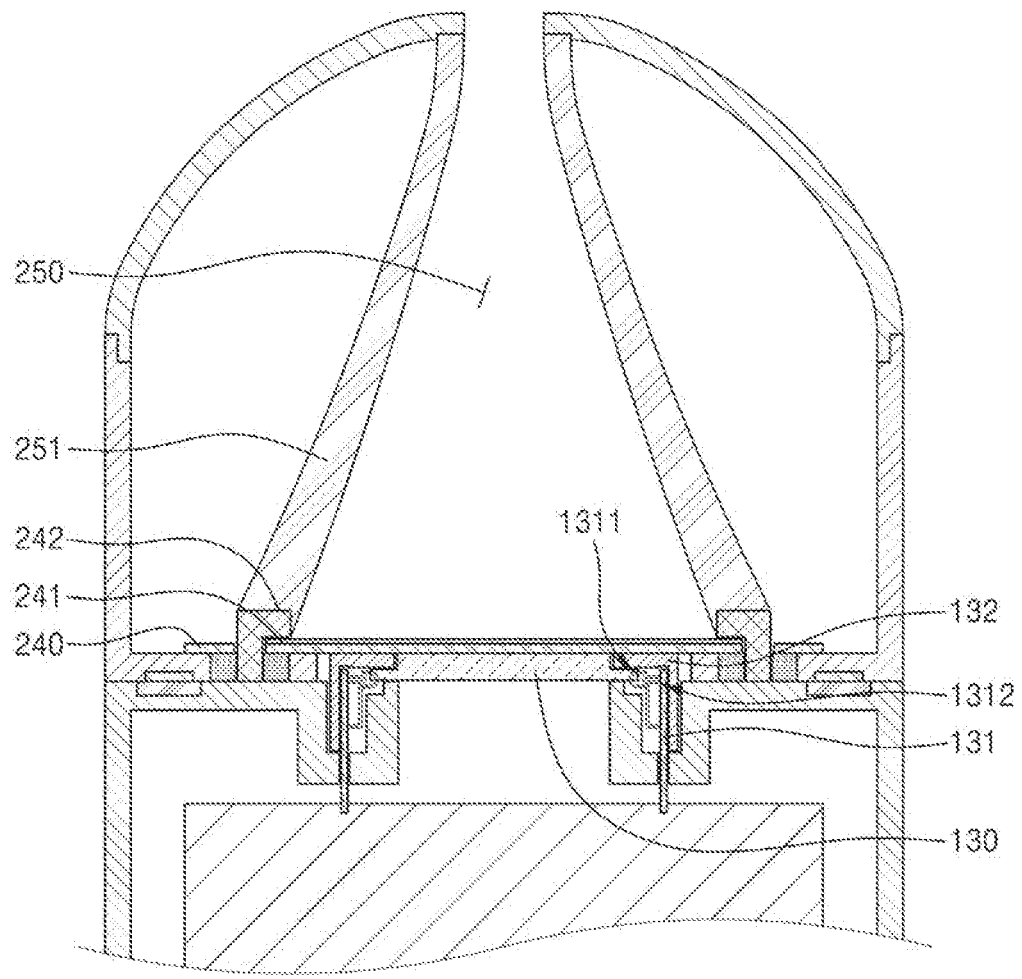
FIG. 6B is a cross-sectional view of a portion of a cartridge shown in FIG. 6A.

FIG. 6A is an enlarged cross-sectional perspective view of a portion in which aerosols are generated in the aerosol generating device according to the embodiment shown in FIG. 5. FIG. 6B is a cross-sectional view of the portion shown in FIG. 6A.

Referring to FIGS. 6A and 6B, the main body 100 may include a connector 131 in an electrical contact with the vibrator 130 to supply power to the vibrator 130, and a vibrator fixing unit 132 for fixing the vibrator 130. In addition, the cartridge 200 may include a liquid delivery member 240, a mesh structure 241, and a fixing member 242.

The connector 131 may include a contact member in contact with the vibrator 130 and an elastic member connected to the contact member and having elasticity. Because the vibrator 130 generates vibration of a high frequency, a contact failure between the vibrator 130 and the connector 131 may occur. Accordingly, the connector 131 may provide a greater contact pressure to the vibrator 130 by the elastic member, and accordingly, the elastic member of the connector 131 may provide a better contact stability between the vibrator 130 and the connector 131.

The vibrator fixing unit 132 is a member for fixing the vibrator 130 to the main body 100. The vibrator fixing unit 132 may fix the vibrator 130 to the main body 100 by pressing a periphery portion of the vibrator 130.

A portion of the liquid delivery member 240 extends into the liquid storage 220. Accordingly, the liquid delivery member 240 may deliver the aerosol generating material accommodated in the liquid storage 220 to the vibrator accommodation space 230.

Because the vibrator accommodation space 230 is formed by an opening 202 formed on the bottom surface of the housing 201, the liquid delivery member 240 may be exposed to the outside through the vibrator accommodation space 230. When the main body 100 and the cartridge 200 are coupled, the vibrator 130 may be accommodated in the vibrator accommodation space 230, and accordingly, the vibrator 130 may contact the liquid delivery member 240. Vibration generated in the vibrator 130 may atomize the aerosol generating material of the liquid delivery member 240, thereby generating aerosols in the cartridge 200.

The mesh structure 241 may include a flat plate and a plurality of holes formed on the plate. The size of the holes may differ according to the embodiments. For example, they may be micro holes having a micro size.

The mesh structure 241 may be stacked on the liquid delivery member 240, such that aerosols must pass through the plurality of holes of the mesh structure 241 to be introduced into the aerosol discharge passage 250. Accordingly, the aerosols may be discharged as fine particles.

In addition, the mesh structure 241 may vibrate together with the vibrator 130 to generate aerosols from the aerosol generating material delivered by the liquid delivery member 240. The mesh structure 241 may be formed of a metal material to vibrate together with the vibrator 130.

The fixing member 242 may be attached to the conduit 251 and fix the liquid delivery member 240 and the mesh structure 241. A detailed configuration of the structure in which the liquid delivery member 240 and the mesh structure 241 are fixed by the fixing member 242 will be described below.

When the main body 100 and the cartridge 200 are coupled, the main body 100 and the cartridge 200 may form a coupled surface. Although not illustrated in FIGS. 6A and 6B, a gap may be formed in the coupled surface of the main body 100 and the cartridge 200, and external air may be introduced through the gap. External air introduced through the gap may be introduced inside the vibrator accommodation space 230 and may be mixed with the aerosol generating material which is vaporized and/or granulated by the vibrator 130.

In addition, external air may be introduced into the vibrator accommodation space 230 by an airflow passage formed on the coupled surface of the main body 100 and the cartridge 200. The airflow passage may be formed to surround the outside of the aerosol discharge passage 250, as described above. For example, the airflow passage may be in fluid communication with the aerosol discharge passage 250, so that external air may be introduced into the aerosol discharge passage 250. A configuration of the airflow passage is not limited to the above description, and any structure in which external air may be introduced may be included without limitation.

FIG. 7 is a partial exploded view of a cartridge according to an embodiment.

Referring to FIG. 7, the housing 201, the liquid delivery member 240, the mesh structure 241 and the fixing member 242 may be sequentially stacked.

As described above, the housing 201 may include the bottom surface including the opening 202 for forming the vibrator accommodation space 230 and the outer wall connected to the mouthpiece 210. A groove 203, in which a protruding portion 242p of the fixing member 242 is accommodated, is formed on the bottom surface of the housing 201.

The fixing member 242 may include the protruding portion 242p for penetrating at least a portion of the liquid delivery member 240. The protruding portion 242p penetrates the liquid delivery member 240 to be coupled to the groove 203, and accordingly, the fixing member 242 may be fixed to the housing 201 while penetrating the liquid delivery member 240 and pressing the periphery portion of the mesh structure 241 at the same time. Accordingly, the fixing member 242 may fix the liquid delivery member 240 and the mesh structure 241.

The groove 203 in which the protruding portion 242p of the fixing member 242 is accommodated may include a sealing member 203s for preventing leakage of the aerosol generating material stored in the liquid storage 220. The sealing member 203s may prevent a gap being formed between the protruding portion 242p and the groove 203. For example, the sealing member 203s may be formed of a soft material such as rubber, silicon, or the like.

Those of ordinary skill in the art related to the present embodiments may understand that various changes in form and details can be made therein without departing from the scope of the characteristics described above. The disclosed methods should be considered in a descriptive sense only and not for purposes of limitation. The scope of the present disclosure is defined by the appended claims rather than by the foregoing description, and all differences within the scope of equivalents thereof should be construed as being included in the present disclosure.

The invention claimed is:

1. A cartridge for an aerosol generating device, comprising:
   a mouthpiece having a discharge hole;
   a liquid storage configured to accommodate an aerosol generating material;
   a vibrator accommodation space configured to accommodate a vibrator of a main body of the aerosol generating device when the cartridge is coupled to the main body; and
   a liquid delivery member configured to deliver the aerosol generating material accommodated in the liquid storage to the vibrator accommodation space such that aerosols are generated from the aerosol generating material by vibration of the vibrator accommodated in the vibrator accommodation space,
   wherein the liquid delivery member is exposed to the outside through the vibrator accommodation space, and contacts the vibrator when the main body and the cartridge are coupled.

2. The cartridge of claim 1, wherein the vibrator accommodation space being disposed on a surface of the cartridge facing the main body.

3. The cartridge of claim 1, further comprising:
   a mesh structure stacked on the liquid delivery member and having a plurality of holes through which aerosols pass to move to the discharge hole.

4. The cartridge of claim 3, wherein the mesh structure vibrates together with the vibrator.

5. The cartridge of claim 3, wherein the mesh structure has a form of a metal flat plate.

6. The cartridge of claim 1, further comprising:
   a conduit connected to the discharge hole of the mouthpiece and forming an aerosol discharge passage through which the aerosols generated by the vibration move toward the discharge hole.

7. The cartridge of claim 6, wherein the conduit has a cross-sectional area decreasing along a direction from the vibrator accommodation space toward the discharge hole.

8. The cartridge of claim 6, further comprising a housing comprising a bottom surface and an outer wall,
   wherein the bottom surface comprises an opening which forms the vibrator accommodation space,
   wherein the outer wall is connected to the mouthpiece, and
   wherein the housing forms an exterior of the cartridge with the mouthpiece.

9. The cartridge of claim 8, further comprising:
   a fixing member attached to the conduit, penetrating at least a portion of the liquid delivery member, and coupled to the housing.

10. The cartridge of claim 8, wherein the liquid storage comprises an inner space formed between the housing and the conduit.

11. The cartridge of claim 1, wherein a gap is formed between the cartridge and the main body when the cartridge is coupled to the main body, such that external air is introduced through the gap.

12. An aerosol generating device comprising:
a main body comprising a vibrator configured to generate vibration; and
a cartridge detachably coupled to the main body,
wherein the cartridge comprises:
a mouthpiece having a discharge hole;
a liquid storage configured to accommodate an aerosol generating material;
a vibrator accommodation space configured to accommodate the vibrator of the main body; and
a liquid delivery member configured to deliver the aerosol generating material accommodated in the liquid storage to the vibrator accommodation space such that aerosols are generated from the aerosol generating material by vibration of the vibrator accommodated in the vibrator accommodation space.

13. The aerosol generating device of claim 12, wherein the main body further comprises a first magnetic body, and
the cartridge further comprises a second magnetic body that is magnetically coupled to the first magnetic body.

14. The aerosol generating device of claim 12, wherein the main body further comprises:
a battery;
a processor configured to control power supplied to the vibrator from the battery; and
a connector configured to transfer power of the battery to the vibrator,
wherein the connector comprises: a contact member in contact with the vibrator; and an elastic member connected to the contact member.

* * * * *